United States Patent [19]

Lutz et al.

[11] Patent Number: 5,717,118
[45] Date of Patent: Feb. 10, 1998

[54] PROCESS FOR PREPARING AMIDO-CARBOXYLIC ACID ESTERS HAVING INTERNAL AMIDE LINKAGES

[75] Inventors: Gary Paul Lutz, Church Hill; George Chester Zima, Kingsport; Thomas Hugh Williams, Fall Branch, all of Tenn.

[73] Assignee: Eastman Chemical Company, Kingsport, Tenn.

[21] Appl. No.: 523,419

[22] Filed: Sep. 5, 1995

[51] Int. Cl.$^6$ .................................................. C07C 231/00
[52] U.S. Cl. ........................... 554/69; 554/63; 564/133; 564/134; 564/135; 564/138
[58] Field of Search .......................... 554/69; 564/133, 564/134, 135, 138

[56] References Cited

U.S. PATENT DOCUMENTS

| | | | |
|---|---|---|---|
| 2,956,068 | 10/1960 | Dohr et al. | 260/404.5 |
| 3,646,061 | 2/1972 | Maeda et al. | 260/326.14 |
| 5,393,901 | 2/1995 | Zima et al. | 554/69 |
| 5,393,902 | 2/1995 | Coope et al. | 554/95 |

FOREIGN PATENT DOCUMENTS

| | | | |
|---|---|---|---|
| 2010601 | of 0000 | France. | |
| 942 864 | 5/1956 | Germany. | |
| 975 633 | 3/1962 | Germany. | |
| 1 184 769 | 1/1965 | Germany. | |
| 1184769 | 1/1965 | Germany | C07C 6/01 |

*Primary Examiner*—Gary Geist
*Assistant Examiner*—Deborah D. Carr
*Attorney, Agent, or Firm*—Michael J. Blake; John D. Thallemer; Harry J. Gwinnell

[57] ABSTRACT

The present invention relates to a one-step process for preparing amido-carboxylic acid esters having the amide nitrogen positioned between two carbonyl carbons by reacting a carboxylic acid or carboxylic acid ester with a monohydric alcohol and either a lactam, amino-carboxylic acid or a polymeric amino-carboxylic acid. In this process, amidation, esterification, alcoholysis, and hydrolysis reactions occur simultaneously.

17 Claims, No Drawings

PROCESS FOR PREPARING AMIDO-CARBOXYLIC ACID ESTERS HAVING INTERNAL AMIDE LINKAGES

FIELD OF THE INVENTION

The present invention relates to a process for preparing amido-carboxylic acid esters having the amide nitrogen positioned between two carbonyl carbons by reacting a carboxylic acid or carboxylic acid ester with a monohydric alcohol and either a lactam, amino-carboxylic acid or a polymeric amino-carboxylic acid.

BACKGROUND OF THE INVENTION

Amido-carboxylic acid esters are industrial intermediates which are used to prepare a number of chemicals in commerce. German Patent No. 1,184,769 discloses a process for preparing amido-carboxylic acid esters by reacting carboxylic acid esters with lactams. The amido carboxylic acid esters derived from this process are limited by the availability of the starting carboxylic acid ester. For example, in order to produce a butyl amido-carboxylic acid ester, a butyl carboxylic acid ester must be prepared in a separate reaction step. The separate reaction step requires longer processing times and results in higher costs. In addition, the process incorporates exotic catalysts and/or high energy radiation.

German Patent No. 975,633 discloses a multi-step process for preparing amido-carboxylic acid esters by forming N-acylated lactams which are reacted with alcohols. The process requires prior formation of N-acylated lactams and the use of acid catalysts. The additional reaction step requires longer processing times and results in higher costs and lower yields.

German Patent No. 942,864 discloses a process for preparing amido-carboxylic acid esters by reacting lactams in acidic alcohol solutions to produce amino-carboxylic acid esters which are reacted with acylating agents to produce amido-carboxylic acid esters. The process requires prior formation of N-acylated lactams and the use of acid catalysts. The additional reaction step requires longer processing times and results in higher costs. The process disclosed in German Patent No. 942,864 is similar to the process disclosed in German Patent No. 975,633 except that the starting lactam in German Patent No. 942,864 is first prepared by a Beckmann rearrangement of an oxime.

What is needed is a simplified process for preparing amido-carboxylic acid esters from readily available starting materials which avoids the need for prior formation of N-acylated lactams.

SUMMARY OF THE INVENTION

The present invention combines amidation, esterification, alcoholysis, and hydrolysis reactions in one step to prepare an amido-carboxylic acid ester having the formula:

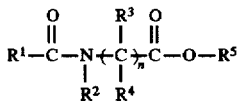

wherein $R^1$ is selected from the group consisting of an alkyl, alkenyl, alkynyl, or cycloalkyl group having 1 to 26 carbon atoms, and an aryl or alkylaryl group having 6 to 14 carbon atoms; $R^2$ is selected from the group consisting of hydrogen, an alkyl, alkenyl, alkynyl, or cycloalkyl group having 1 to 10 carbon atoms, and an aryl or alkylaryl group having 6 to 10 carbon atoms; $R^3$ and $R^4$ are independently selected from the group consisting of hydrogen, halogen, an alkyl, alkenyl, alkynyl, cycloalkyl, or alkoxy group having 1 to 10 carbon atoms, and aryl or alkylaryl groups having 6 to 10 carbon atoms; $R^5$ is selected from the group consisting of an alkyl, alkenyl, alkynyl, or cycloalkyl group having 1 to 6 carbon atoms, and aryl or alkylaryl group having 6 to 10 carbon atoms; and n is an integer from 1 to 12;

said process comprising reacting at a temperature of 150° C. to 300° C. at the autogenic pressure for 0.5 to 15 hours, a mixture containing (1) a carboxylic acid or carboxylic acid ester having the formula:

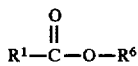

wherein $R^1$ is defined as above and $R^6$ is a hydrogen atom or an alkyl, alkenyl, alkynyl, or cycloalkyl group containing from 1 to 6 carbon atoms or an aryl or alkylaryl group containing from 6 to 10 carbon atoms;

(2) a nitrogen containing compound selected from the group consisting of

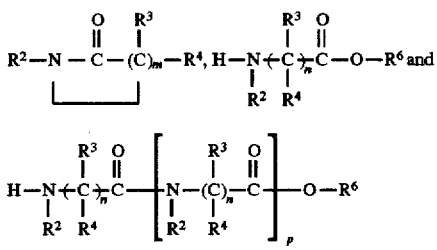

wherein $R^1$, $R^2$, $R^3$, $R^4$, $R^6$ and n are defined as above and m is an integer from 1 to 12 and p is an integer greater than or equal to 1; and (3) a monohydric alcohol having the formula:

wherein $R^5$ is defined as above, provided the carboxylic acid or carboxylic acid ester, nitrogen containing compound and monohydric alcohol are present in a molar ratio of 1–5:0.5–2:2–50, respectively.

DESCRIPTION OF THE INVENTION

The present invention relates to a process for preparing an amido-carboxylic acid ester having an internal amide linkage wherein the amide nitrogen is positioned between two carbonyl carbons. The process involves the simultaneous occurrence of multiple reactions such as amidation, esterification, alcoholysis, and hydrolysis. The amido-carboxylic acid ester having an internal amide linkage has the formula:

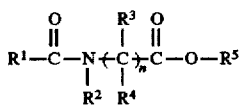

In the above formula for the amido-carboxylic acid ester, $R^1$ is selected from an alkyl, alkenyl, alkynyl, or cycloalkyl group having 1 to 26 carbon atoms, or an aryl or alkylaryl group having 6 to 14 carbon atoms. $R^2$ is selected from hydrogen, or an alkyl, alkenyl, alkynyl, or cycloalkyl group having 1 to 10 carbon atoms, or an aryl or alkylaryl group having 6 to 10 carbon atoms. $R^3$ and $R^4$ are independently selected from hydrogen, halogen, or an alkyl, alkenyl, alkynyl, cycloalkyl, or alkoxy group having 1 to 10 carbon atoms, or an aryl or alkylaryl groups having 6 to 10 carbon atoms. $R^5$ is selected from an alkyl, alkenyl, alkynyl, or cycloalkyl group having 1 to 6 carbon atoms, or an aryl or alkylaryl group having 6 to 10 carbon atoms. The letter n is an integer from 1 to 12.

The amido-carboxylic acid ester is prepared by reacting at a temperature of 150° C. to 300° C., preferably 180° C. to 250° C., and at the autogenic pressure for 0.5 hours to 15 hours, preferably 1 hour to 10 hours, in a suitable reactor such as an autoclave, a mixture containing a carboxylic acid or carboxylic acid ester, a nitrogen containing compound, and a monohydric alcohol.

The carboxylic acid or carboxylic acid ester, component (1), has the formula:

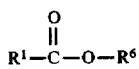

In the carboxylic acid or carboxylic acid ester formula, $R^1$ is defined as above and $R^6$ is a hydrogen atom or an alkyl, alkenyl, alkynyl, or cycloalkyl group having 1 to 6 carbon atoms or an aryl or alkylaryl group having 6 to 10 carbon atoms. The carboxylic acid has 2 to 27 carbon atoms, preferably 6 to 20, and most preferably 8 to 14 carbon atoms. The carboxylic acid may contain straight, branched or cyclic chains, may be of natural or synthetic origin, and may be of a saturated or unsaturated nature. The carboxylic acid esters are derived from the above carboxylic acids and may include, but are not limited to, the methyl, ethyl, propyl, isopropyl and butyl ester of the carboxylic acid. The carboxylic acids and carboxylic acid esters thereof may be used in pure form or else in the form of their mixtures as commercially available.

Examples of carboxylic acids are: caproic acid, heptanoic acid, caprylic acid, 2-ethylhexanoic acid, pelargonic acid, capric acid, undecylic acid, lauric acid, palmitic acid, stearic acid, oleic acid, linoleic acid, behenic acid, benzoic acid, phenylacetic acid, cinamic acid, and the like. Preferred carboxylic acids are: caproic acid, heptanoic acid, caprylic acid, 2-ethylhexanoic acid, perlargonic acid, capric acid, undecylic acid, and lauric acid. Examples of carboxylic acid esters are: methyl, ethyl, propyl, isopropyl, butyl, isobutyl, sec-butyl, and tert-butyl esters of caproic acid, heptanoic acid, caprylic acid, 2-ethylhexanoic acid, perlargonic acid, capric acid, undecylic acid, lauric acid, palmitic acid, stearic acid, oleic acid, linoleic acid, behenic acid, benzoic acid, phenylacetic acid, cinamic acid, and the like.

The nitrogen containing compound, component (2), is selected from a lactam, an amino-carboxylic acid, and a polymeric amino-carboxylic acid. Lactams useful in the process of this invention have the formula:

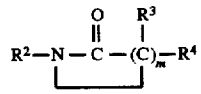

In the formula for the lactam, $R^2$ is selected from hydrogen, or an alkyl, alkenyl, alkynyl, or cycloalkyl group having 1 to 10 carbon atoms, or an aryl or alkylaryl group having 6 to 10 carbon atoms. $R^3$ and $R^4$ are independently selected from hydrogen, halogen, or an alkyl, alkenyl, alkynyl, cycloalkyl, or alkoxy group having 1 to 10 carbon atoms, or an aryl or alkylaryl group having 6 to 10 carbon atoms. The letter m is an integer from 1 to 12. Suitable lactams include butyrolactam, γ-valerolactam, δ-valerolactam, γ-caprolactam, δ-caprolactam, ε-caprolactam, β-propiolactam, and similar lactams. Preferably, the lactam contains 3 to 7 carbon atoms in the lactam ring. The lactam may be substituted at the nitrogen atom by lower hydrocarbon radicals containing 1 to 10 carbon atoms. For example, N-substituted lactams where the substituent is methyl, ethyl, propyl, isopropyl, butyl, sec-butyl, tert-butyl, phenyl, and benzyl, may be used.

Amino-carboxylic acids useful in the process of this invention have the formula:

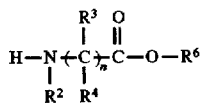

In the formula for the amino-carboxylic acid, $R^2$ is selected from hydrogen, or an alkyl, alkenyl, alkynyl, or cycloalkyl group having 1 to 10 carbon atoms, or an aryl or alkylaryl group having 6 to 10 carbon atoms. $R^3$ and $R^4$ are independently selected from hydrogen, halogen, or an alkyl, alkenyl, alkynyl, cycloalkyl, or alkoxy group having 1 to 10 carbon atoms, or an aryl or alkylaryl group having 6 to 10 carbon atoms. $R^6$ is hydrogen or an alkyl, alkenyl, alkynyl, or cycloalkyl group having 1 to 6 carbon atoms, or an aryl or alkylaryl group having 6 to 10 carbon atoms. The letter n is an integer from 1 to 12, preferably 2 to 7. Examples of amino-carboxylic acids are: glycine, alanine, 3-aminopropionic acid, 4-aminobutyric acid, 5-aminopentanoic acid, 6-aminohexanoic acid, 7-aminoheptanoic acid, and the like. Suitable amino-carboxylic acids also include N-substituted amino-carboxylic acids where the substituent is methyl, ethyl, propyl, isopropyl, butyl, sec-butyl, tert-butyl, phenyl, benzyl, and the like.

Polymeric amino-carboxylic acids useful in the process of this invention have the formula:

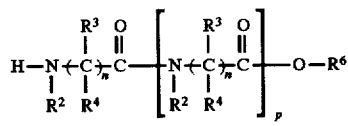

In the formula for the polymeric amino-carboxylic acid, $R^2$ is selected from hydrogen, or an alkyl, alkenyl, alkynyl, or cycloalkyl group having 1 to 10 carbon atoms, or an aryl or alkylaryl group having 6 to 10 carbon atoms. $R^3$ and $R^4$ are independently selected from hydrogen, halogen, or an alkyl, alkenyl, alkynyl, cycloalkyl, or alkoxy group having 1 to 10 carbon atoms, or an aryl or alkylaryl group having 6 to 10 carbon atoms. $R^6$ is a hydrogen atom or an alkyl, alkenyl, alkynyl, or cycloalkyl group having 1 to 6 carbon atoms or an aryl or alkylaryl group having 6 to 10 carbon atoms. The letter n is an integer from 1 to 12. The letter p is an integer greater than or equal to 1.

Examples of polymeric amino-carboxylic acids are: poly (glycine), poly(alanine), poly(3-aminopropionic acid), poly (4-aminobutyric acid), poly(5-aminopentanoic acid), poly (6-aminohexanoic acid) [NYLON-6], poly(7-aminoheptanoic acid), poly(11-aminoundecanoic acid) [NYLON-11], poly(12-aminododecanoic acid) [NYLON-12], and the like. Suitable polymeric amino-carboxylic acids also include N-substituted polymeric amino-carboxylic acids where the substituent is methyl, ethyl, propyl, isopropyl, butyl, sec-butyl, tert-butyl, phenyl, benzyl, and the like.

The monohydric alcohol, component (3), has the formula:

$$HO-R^5$$

In the formula for the monohydric alcohol, $R^5$ is selected from an alkyl, alkenyl, alkynyl, or cycloalkyl group having 1 to 6 carbon atoms, or an aryl or alkylaryl group having 6 to 10 carbon atoms. The monohydric alcohol is selected from aliphatic alcohols including paraffinic and olefinic alcohols, alicyclic alcohols, and aromatic alcohols. Examples of suitable monohydric alcohols include methanol, ethanol, propanol, isopropanol, n-butanol, sec-butanol, tert-butanol, pentanol, hexanol, cyclohexanol, phenol, cyclopentanol, 2-phenylethanol, 4-methylpentan-1-ol, benzyl alcohol, and the like. Preferably, the monohydric alcohol is methanol, ethanol, propanol, isopropanol, and butanol.

Optionally, water may be added to the process in a catalytic amount of 0.01 to 5 weight percent. The water acts as a hydrolysis agent and speeds up the rate of the reaction. Any source of water may be used including tap water, distilled water, and water that is present in any other component of the reaction mixture. Distilled water is preferred since tap water may contain metal salts which in combination with the carboxylic acid could form surface active agents and inhibit isolation of the amido-carboxylic acid ester product.

The mixture containing amido-carboxylic acid esters produced by the process of the present invention contains amido-carboxylic acid ester product as well as unreacted starting materials and other by-products such as water, oligomeric amido-carboxylic acid, and oligomeric amido-carboxylic acid ester.

Purification of the reaction mixture to recover the amido-carboxylic acid ester product is accomplished by methods known in the art such as distillation, extraction, crystallization or a combination thereof. Since the multiple reactions are conducted simultaneously in the reactor, all of the unreacted starting materials and byproducts including amido-carboxylic acids, oligomeric amido-carboxylic acids, and oligomeric amido-carboxylic acid esters, can be recycled back to the reactor after the desired amido-carboxylic acid ester has been removed from the crude reaction mixture. An example of a purification scheme would be a two-stage distillation. In the first distillation stage, low boiling components such as alcohol, lactam, carboxylic acid ester, carboxylic acid, and water are removed from the reaction mixture to provide an amido-carboxylic acid ester rich residue. In the second distillation stage, the temperature is increased, the pressure is decreased and the desired amido-carboxylic acid ester product is removed from the amido-carboxylic acid ester rich residue produced in the first stage of the distillation. The high boiling material which remains when the amido-carboxylic acid ester product is removed from the amido-carboxylic acid ester rich residue contains high levels of high boiling components such as oligomeric amido-carboxylic acids and oligomeric amido-carboxylic esters. The low boiling components removed from the first stage of the distillation and the high boiling components remaining after the amido-carboxylic acid ester product is isolated from the second stage of the distillation can be recycled back to the reactor.

The process of the present invention will be further illustrated by a consideration of the following examples, which are intended to be exemplary of the invention.

EXAMPLES 1–9

Examples 1–9 describe the preparation of amido-carboxylic acid esters. In Examples 1–8, component (1) was octanoic acid or methyl octanoate, component (2) was caprolactam or NYLON-6, and component (3) was methanol. In Example 9, component (4) which is water was added. The relative weight ratios, mole equivalents of the starting materials, and reaction times for preparing the amido-carboxylic acid esters are summarized in Table I. The composition of amido-carboxylic acid ester reaction mixture prepared in Examples 1–9 are summarized in Table II.

In each example, the amido-carboxylic acid esters were prepared by reacting either octanoic acid or methyl octanoate with caprolactam or Nylon-6 in the presence of methanol and in one case a catalytic amount of water. The reactions were carried out at ~230° C. at autogenic pressure for a period of time indicated in Table I, in a rocking autoclave. The reaction mixture was allowed to cool to 25° C. and subsequently analyzed using gas chromatography.

In Examples 1, 2, and 3, the ratio of methanol and octanoic acid to caprolactam were varied. Example 4 used the same components of Example 3 with the exception that a portion of the octanoic acid was replaced with methyl octanoate. Example 5 used the same components of Example 3 with the exception that all of the octanoic acid was replaced with methyl octanoate.

Example 6 used the same components of Example 3 with the exception that caprolactam was replaced with NYLON-6. Example 7 used the same components of Example 6 with the exception that octanoic acid was replaced with methyl octanoate. Example 8 was a repeat of Example 7 with the exception that the reaction time was increased from 1 to 8 hours. Example 9 used the same components of Example 7 with the exception that water was added.

The reaction mixtures prepared in Examples 1–9 were analyzed by two separate gas chromatography methods. The reaction mixtures contained amido-carboxylic acid esters as well as unreacted starting materials and other by-products which included: water, methanol, oligomeric amido-carboxylic acid, and oligomeric amido-carboxylic acid ester. The first method was used to determine the relative amounts of methanol, methyl octanoate, and water contained in the liquid fraction of each reaction mixture prepared in the examples. The second method reacted each reaction mixture with a silylating reagent before injection and was used to determine the relative amounts of caprolactam, octanoic acid, methyl octanoate, amido-carboxylic acid ester (mono), diamido-carboxylic acid ester, and triamido acid ester in each reaction mixture prepared in the examples.

Some of the reaction mixtures contained solids. The solids were filtered from the reaction mixtures to determine the relative weight percent and are reported as Nylon-6 in Table II. The data in Table II is relative area percent. Chromatograms which contained peaks consistent with mono-, di-, or triamido-carboxylic acid ester also contained peaks assignable as mono-, di-, or triamido-carboxylic acid. The values in Table II for mono-, di-, and triamido-carboxylic acid ester result from adding the area of the small mono-, di-, and triamido-carboxylic acid peaks to the area of the corresponding mono-, di-, and triamido-carboxylic acid ester peaks.

TABLE I

RELATIVE WEIGHT PERCENT OF STARTING MATERIALS

| Ex. | Components | | | | | | Time |
|---|---|---|---|---|---|---|---|
| | 1 | 2 | 3 | 4 | 5 | 6 | |
| 1 | 22.2 [1] | — | 28.3 [1] | — | 49.5 [7.9] | — | 1 hr |
| 2 | 13.1 [1] | — | 16.6 [1] | — | 70.3 [19] | — | 1 hr |
| 3 | 9.2 [1] | — | 41.4 [3.5] | — | 49.4 [19] | — | 1 hr |
| 4 | 9.2 [1] | — | 11.7 [1] | 29.7 [2.3] | 49.4 [19] | — | 1 hr |
| 5 | 9.2 [1] | — | — | 41.4 [3.2] | 49.4 [19] | — | 1 hr |
| 6 | — | 9.2 [1] | 41.4 [3.5] | — | 49.4 [19] | — | 1 hr |
| 7 | — | 9.2 [1] | — | 41.4 [3.2] | 49.4 [19] | — | 1 hr |
| 8 | — | 9.2 [1] | — | 41.4 [3.2] | 49.4 [19] | — | 8 hr |
| 9 | — | 9 [1] | — | 40.8 [3.2] | 48.7 [19] | 1.5 [1] | 1 hr |

1 = Caprolactam
2 = NYLON-6
3 = Octanoic Acid
4 = Methyl Octanoate
5 = Methanol
6 = Water
Numbers in brackets [ ] are the relative mole equivalents of that component.

TABLE II

COMPOSITION OF REACTION MIXTURE (AREA %)

| Ex. | Component | | | | | | | | |
|---|---|---|---|---|---|---|---|---|---|
| | 1 | 2* | 3 | 4 | 5 | 6 | 7 | 8 | 9 |
| 1 | 9.4 | 2 | 2 | 21.5 | 46.7 | 3.4 | 9.4 | 4 | 1.6 |
| 2 | 9.7 | — | 1.4 | 13.4 | 68.2 | 1.9 | 3.7 | 1.3 | 0.4 |
| 3 | 8.3† | — | † | 37.8 | 41.6 | 4.6 | 6.5 | 1.2 | — |
| 4 | 7.5† | — | † | 37 | 47.3 | 1.1 | 5.9 | 1.2 | — |
| 5 | 6.6† | — | † | 41.4 | 49.6 | 0.4 | 1.8 | 0.2 | — |
| 6 | 1.8 | 0.2 | 5.2 | 39 | 42.4 | 4.5 | 4.9 | 1.7 | 0.3 |
| 7 | 1.1 | 10.2 | — | 42.7 | 45.7 | 0.2 | 0.04 | — | — |
| 8 | 0.9 | 0.1 | 1.5 | 42.8 | 49.2 | 1.1 | 3.1 | 1.1 | 0.2 |
| 9 | 2.2† | 3.9 | † | 447 | 47 | 1.9 | 0.3 | — | — |

1 = Caprolactam
2 = NYLON-6
3 = Octanoic Acid
4 = Methyl Octanoate
5 = Methanol
6 = Water
7 = Amido-carboxylic Acid Ester
8 = Diamido-carboxylic Acid Ester
9 = Triamido-carboxylic Acid Ester
*Represents the approximate weight percent of solids (NYLON-6) contained in the reaction mixture.
†Octanoic acid and caprolactam co-eluted and are treated as 100% caprolactam.

The results in Table II indicate that the ratio of amido-carboxylic acid ester to diamido-carboxylic acid ester is dependent on the ratio of methanol to caprolactam (Examples 1 and 2) and on the ratio of octanoic acid to caprolactam (Examples 2 and 3). The ratio of amido-carboxylic acid ester to diamido-carboxylic acid ester increases from 2.4 (Example 1) to 2.8 (Example 2) to 5.4 (Example 3). Examples 4 and 5 illustrate that octanoic acid increases the fraction of amido-carboxylic acid ester obtained. The octanoic acid acts as a catalyst or as a source of water to accelerate the reaction.

Example 6 demonstrates that NYLON-6, a polymeric material, can be substituted for caprolactam to obtain results similar to those in Examples 1–3. Examples 7 and 8 demonstrate that the reaction of NYLON-6 with methyl octanoate is much slower than the corresponding reaction with octanoic acid in Example 6. Example 9 indicates that the addition of water accelerates the reaction of the methyl octanoate as compared with Example 7. However, the rate of reaction in Example 9 is slower than with octanoic acid in Example 6. The advantages of the process of this invention are that amidation, alcoholysis, esterification, and hydrolysis, are carried out simultaneously, thus reducing the number of reaction steps and pieces of equipment necessary to prepare amido-carboxylic acid esters, and allowing efficient recycling of oligomeric materials generated during the reaction. In addition, the reaction of oligomeric or polymeric amido-carboxylic acids or esters and oligomeric or polymeric amino-carboxylic acids or esters allows for recycling and the potential use of oligomeric or polymeric waste materials from the production of polymers such as NYLON-6. Moreover, the versatility of the reaction is enhanced by the ability to use a variety of starting materials to obtain a given amido-carboxylic acid ester.

Many variations will suggest themselves to those skilled in this art in light of the above detailed description. All such obvious modifications are within the full intended scope of the appended claims.

What is claimed is:

1. A process for preparing an amido-carboxylic acid ester having the formula:

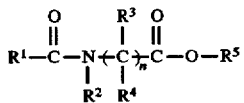

wherein $R^1$ is selected from the group consisting of an alkyl, alkenyl, alkynyl, or cycloalkyl group having 1 to 26 carbon atoms, and an aryl or alkylaryl group having 6 to 14 carbon atoms; $R^2$ is selected from the group consisting of hydrogen, an alkyl, alkenyl, alkynyl, or cycloalkyl group having 1 to 10 carbon atoms, and an aryl or alkylaryl group having 6 to 10 carbon atoms; $R^3$ and $R^4$ are independently selected from the group consisting of hydrogen, halogen, an alkyl, alkenyl, alkynyl, cycloalkyl, or alkoxy group having 1 to 10 carbon atoms, and aryl or alkylaryl groups having 6 to 10 carbon atoms; $R^5$ is selected from the group consisting of an alkyl, alkenyl, alkynyl, or cycloalkyl group having 1 to 6 carbon atoms, and aryl or alkylaryl group having 6 to 10 carbon atoms; and n is an integer from 1 to 12;
said process comprising reacting at a temperature of 150° C. to 300° C. at the autogenic pressure for 0.5 to 15 hours, a mixture containing (1) a carboxylic acid or carboxylic acid ester having the formula:

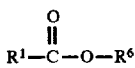

wherein $R^1$ is defined as above and $R^6$ is a hydrogen atom or an alkyl, alkenyl, alkynyl, or cycloalkyl group containing from 1 to 6 carbon atoms or an aryl or alkylaryl group containing from 6 to 10 carbon atoms;

(2) a nitrogen containing compound selected from the group consisting of

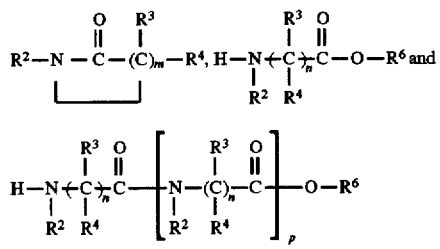

wherein $R^1$, $R^2$, $R^3$, $R^4$, $R^6$ and n are defined as above, and m is an integer from 1 to 12 and p is an integer greater than or equal to 1; and (3) a monohydric alcohol having the formula:

wherein $R^5$ is defined as above, provided the carboxylic acid or carboxylic acid ester, nitrogen containing compound and monohydric alcohol are present in a molar ratio of 1–5:0.5–2:2–50, respectively.

2. The process of claim 1 which additionally contains 0.01 to 5 weight percent of water.

3. The process of claim 1 wherein the amido-carboxylic acid ester is prepared by reacting at a temperature of 180° C. to 250° C., and at the autogenic pressure for 1 hour to 10 hours.

4. The process of claim 1 wherein the carboxylic acid, component (1), is selected from the group consisting of caproic acid, heptanoic acid, caprylic acid, 2-ethylhexanoic acid, pelargonic acid, capric acid, undecylic acid, lauric acid, palmitic acid, stearic acid, oleic acid, linoleic acid, behenic acid, benzoic acid, phenylacetic acid, and cinamic acid.

5. The process of claim 1 wherein the carboxylic acid ester, component (1), is selected from the group consisting of methyl, ethyl, propyl, isopropyl, butyl, isobutyl, sec-butyl, and tert-butyl esters of caproic acid, heptanoic acid, caprylic acid, 2-ethylhexanoic acid, perlargonic acid, capric acid, undecylic acid, lauric acid, palmitic acid, stearic acid, oleic acid, linoleic acid, behenic acid, benzoic acid, phenylacetic acid, and cinamic acid.

6. The process of claim 1 wherein the carboxylic acid ester, component (1), is selected from the group consisting of methyl octanoate, methyl decanoate, and methyl nonanoate.

7. The process of claim 1 wherein the nitrogen containing compound, component (2), is selected from the group consisting of a lactam, an amino-carboxylic acid, and a polymeric amino-carboxylic acid.

8. The process of claim 7 wherein the lactam is selected from the group consisting of butyrolactam, γ-valerolactam, δ-valerolactam, γ-caprolactam, δ-caprolactam, ε-caprolactam, and β-propiolactam.

9. The process of claim 8 wherein the lactam is γ-caprolactam.

10. The process of claim 7 wherein the amino-carboxylic acid is selected from the group consisting of glycine, alanine, 3-aminopropionic acid, 4-aminobutyric acid, 5-aminopentanoic acid, 6-aminohexanoic acid, and 7-aminoheptanoic acid.

11. The process of claim 10 wherein the amino-carboxylic acid is 6-aminohexanoic acid.

12. The process of claim 1 wherein the polymeric amino-carboxylic acid is selected from the group consisting of poly(glycine), poly(alanine), poly(3-aminopropionic acid), poly(4-aminobutyric acid), poly(5-aminopentanoic acid), poly(6-aminohexanoic acid), poly(7-aminoheptanoic acid), poly(11-aminoundecanoic acid), and poly(12-aminododecanoic acid).

13. The process of claim 12 wherein the polymeric amino-carboxylic acid is poly(6-aminohexanoic acid).

14. The process of claim 1 wherein the monohydric alcohol, component (3), is selected from the group consisting of aliphatic alcohols, alicyclic alcohols, and aromatic alcohols.

15. The process of claim 14 wherein the monohydric alcohol is selected from the group consisting of methanol, ethanol, propanol, isopropanol, n-butanol, sec-butanol, tert-butanol, pentanol, hexanol, cyclohexanol, phenol, cyclopentanol, 2-phenylethanol, 4-methylpentan-1-ol, and benzyl alcohol.

16. The process of claim 15 wherein the monohydric alcohol is selected from the group consisting of methanol, ethanol, propanol, isopropanol, and butanol.

17. The process of claim 1 which additionally comprises a purification step for the amido carboxylic acid ester.

* * * * *